(12) United States Patent
Yonezu et al.

(10) Patent No.: US 10,067,106 B2
(45) Date of Patent: Sep. 4, 2018

(54) SENSOR

(71) Applicant: NGK SPARK PLUG CO., LTD., Nagoya-shi, Aichi (JP)

(72) Inventors: Kunihiko Yonezu, Inuyama (JP); Takehiro Oba, Kounan (JP); Hisaharu Nishio, Tokai (JP); Ginjiro Ito, Nagoya (JP); Yuichi Yamada, Komaki (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 217 days.

(21) Appl. No.: 14/991,017

(22) Filed: Jan. 8, 2016

(65) Prior Publication Data
US 2016/0202226 A1    Jul. 14, 2016

(30) Foreign Application Priority Data

Jan. 9, 2015   (JP) .................................. 2015-002893
Oct. 15, 2015  (JP) .................................. 2015-203454

(51) Int. Cl.
*G01N 33/00* (2006.01)
*F01N 13/00* (2010.01)
*F02M 35/10* (2006.01)

(52) U.S. Cl.
CPC ....... *G01N 33/0036* (2013.01); *F01N 13/008* (2013.01); *F02M 35/10373* (2013.01)

(58) Field of Classification Search
CPC .............. G01N 33/0036; F01N 13/008; F02M 35/10373; H01R 11/18; H01R 13/2442
USPC ................... 73/23.31, 23.32; 204/424–431
See application file for complete search history.

(56) References Cited

U.S. PATENT DOCUMENTS

| | | | |
|---|---|---|---|
| 6,068,746 A | 5/2000 | Kojima et al. | |
| 2014/0020446 A1 | 1/2014 | Yonezu et al. | |

FOREIGN PATENT DOCUMENTS

| | | |
|---|---|---|
| JP | 3873390 B2 | 1/2007 |
| JP | 2013-195277 A | 9/2013 |
| JP | 2014-2132 A | 1/2014 |
| JP | 2014-38083 A | 2/2014 |

*Primary Examiner* — Lisa Caputo
*Assistant Examiner* — Irving A Campbell
(74) *Attorney, Agent, or Firm* — Sughrue Mion, PLLC

(57) ABSTRACT

A sensor includes a detector element, a connection terminal, and a separator. The contacting portion is in contact with a conductive member so as to overlap the conductive member in a thickness direction, which is a direction of thickness of the detector element between the principal surfaces. The separator includes an element accommodation space that accommodates a portion of an element contact portion and an element back portion, and a partition wall that separates the element accommodation space from a terminal accommodation space that accommodates the contacting portion and a portion of the conductive member and that is adjacent to the element accommodation space in the thickness direction. A frame main body is disposed in an element-side region, which is a region on an element-accommodation-space side in the thickness direction in a region obtained by extending the terminal accommodation space toward the front side in the axial direction.

4 Claims, 10 Drawing Sheets

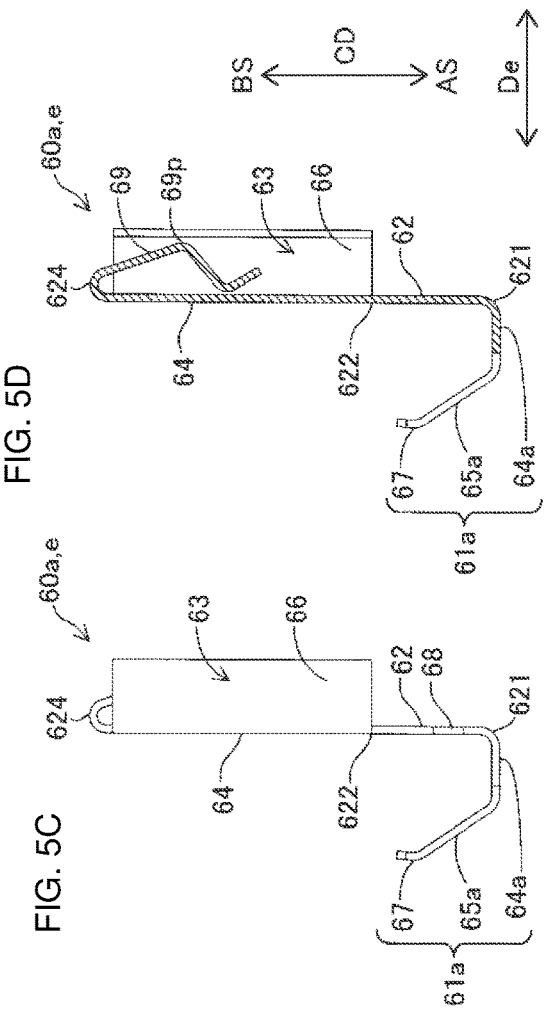

SENSOR

TECHNICAL FIELD

The present invention relates to a sensor.

BACKGROUND ART

Gas sensors attached to inlet systems or exhaust systems of internal combustion engines (for example, diesel engines or gasoline engines) are known. Such a gas sensor is used to detect the concentration of a specific gas component (for example, oxygen or Nox) contained in measurement target gas (see, for example, PTL 1). The gas sensor disclosed in PTL 1 includes a detector element that extends in an axial direction, connection terminals, and a separator. The detector element includes a detection portion that is disposed at a front side and through which a current corresponding to the oxygen concentration flows and electrical pads that are disposed at a back side and that are in contact with the connection terminals. Each connection terminal includes a frame main body that extends in the axial direction, a contacting portion that extends from a back end portion of the frame main body toward the back side and that is in contact with a conductive member, and an element contact portion that is bent at a front end portion of the frame main body so as to extend toward the back side and that is in elastic contact with a corresponding one of the electrical pads. The conductive member is electrically connected to an external circuit for calculating a specific gas component on the basis of a signal output from the detector element. The separator accommodates at least a portion of each connection terminal and at least a back portion of the detector element.

CITATION LIST

Patent Literature

[PTL 1] Japanese Unexamined Patent Application Publication No. 2014-38083

SUMMARY OF INVENTION

Technical Problem

In the above-described technology of the related art, when the distance between the frame main body and the detector element in a thickness direction of the detector element is large, the length of the element contact portion that extends from the frame main body (contact distance) needs to be increased to bring the element contact portion in contact with the corresponding electrical pad. When the length of the element contact portion is increased, there is a risk that the pressing force (spring force) applied by the element contact portion will be reduced when the element contact portion is in elastic contact with the corresponding electrical pad. Accordingly, there has been a demand for technology capable of suppressing a reduction in the pressing force applied by the element contact portion.

Solution to Problem

The present invention has been made to solve the above-described problems, and may be realized by the following embodiments or applications.

(1) According to an aspect of the present invention, a sensor includes a detector element that extends in an axial direction and has a shape of a plate having two opposing principal surfaces, the detector element including a detection portion at a front side in the axial direction and an element back portion at a back side in the axial direction, the detection portion detecting a specific gas component contained in measurement target gas, the element back portion having an electrical pad formed on at least one of the two principal surfaces; a connection terminal which includes an oblong frame main body that extends in the axial direction, an element contact portion that is bent at a front end portion of the frame main body so as to extend toward the detector element and toward the back side and that is in elastic contact with the electrical pad, and a contacting portion that extends from a back end portion of the frame main body toward the back side and that is in contact with a conductive member that is electrically connected to an external circuit; and a separator that accommodates at least a portion of the connection terminal and at least a portion of the element back portion. The contacting portion is in contact with the conductive member so as to overlap the conductive member in a thickness direction, which is a direction of thickness of the detector element between the principal surfaces. The separator includes a partition wall that separates an element accommodation space and a terminal accommodation space from each other, the element accommodation space accommodating a portion of the element contact portion and the element back portion, the terminal accommodation space accommodating the contacting portion and a portion of the conductive member and being adjacent to the element accommodation space in the thickness direction. The frame main body is disposed in an element-side region, which is a region on an element-accommodation-space side in the thickness direction in a region obtained by extending the terminal accommodation space toward the front side in the axial direction.

According to this aspect, since the frame main body is disposed in the element-side region in the terminal accommodation space, the distance between the detector element and the frame main body in the thickness direction can be reduced. Accordingly, the distance from an end of the element contact portion that is connected to the frame main body to the electrical pad can be reduced. Therefore, a reduction in the pressing force applied by the element contact portion to the electrical pad when the element contact portion is in elastic contact with the electrical pad can be suppressed.

(2) In the above-described sensor, the contacting portion may surround a periphery of the conductive member or be surrounded by the conductive member at a periphery of the contacting portion, so that the contacting portion is in contact with the conductive member so as to overlap the conductive member in the thickness direction.

In this case, the contacting portion and the conductive member are in contact with each other so as to overlap in the thickness direction. Therefore, the reliability of electrical connection between the contacting portion and the conductive member is increased.

The present invention can be embodied in various forms. For example, the present invention may be embodied not only as the gas sensor but also as a method for manufacturing the gas sensor, or a connection terminal.

BRIEF DESCRIPTION OF DRAWINGS

FIGS. 5A to 5D illustrate first and fifth connection terminals.

DESCRIPTION OF EMBODIMENTS

A. First Embodiment

Figure 1:
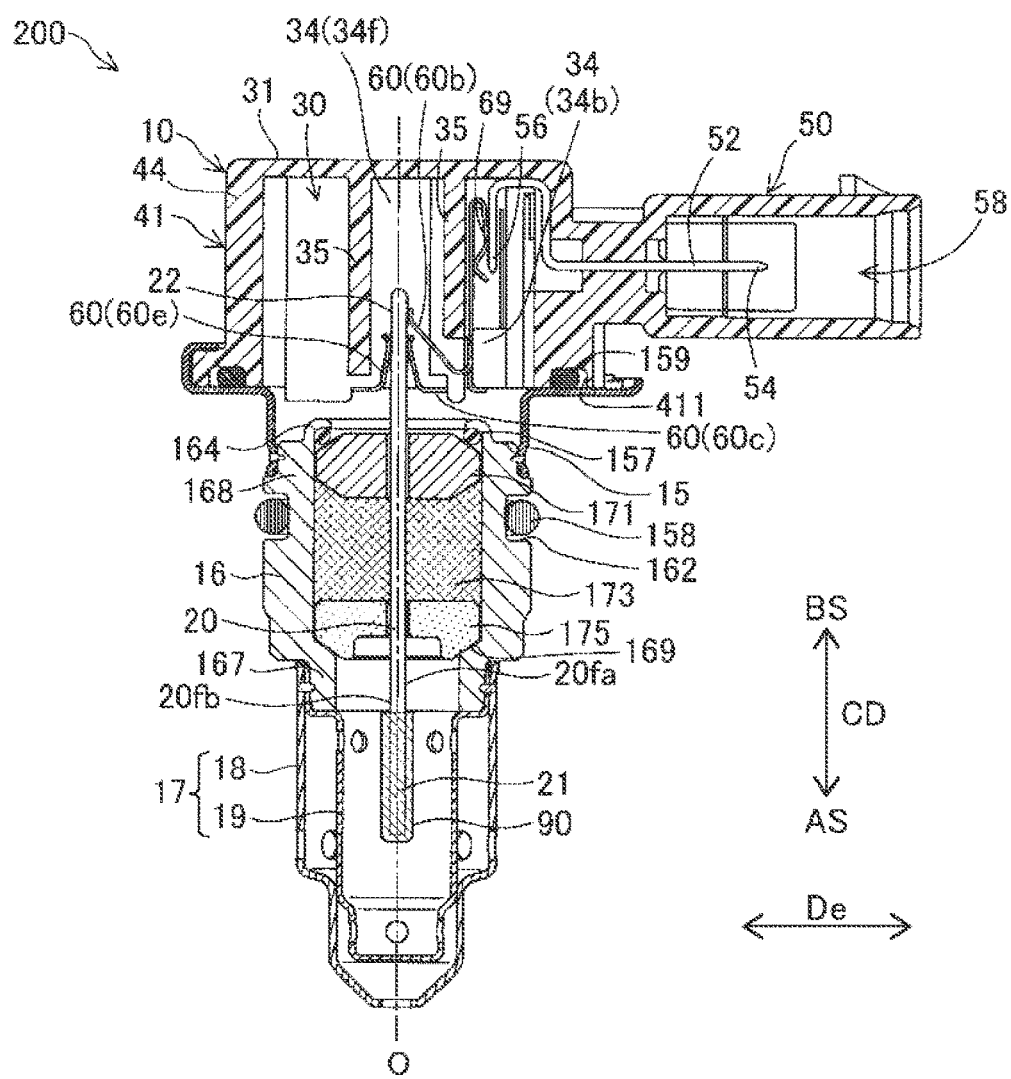
FIG. 1 is a sectional view of a gas sensor according to a first embodiment of the present invention.
Figure 2:
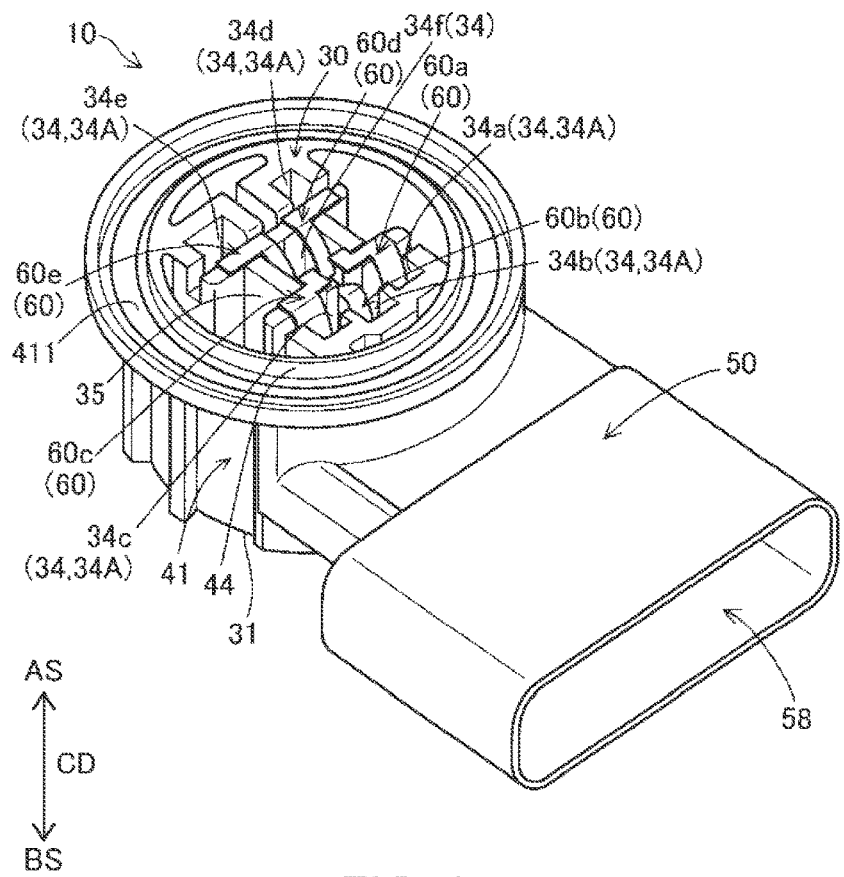
FIG. 2 is a perspective view of a terminal accommodation unit.
Figure 3:
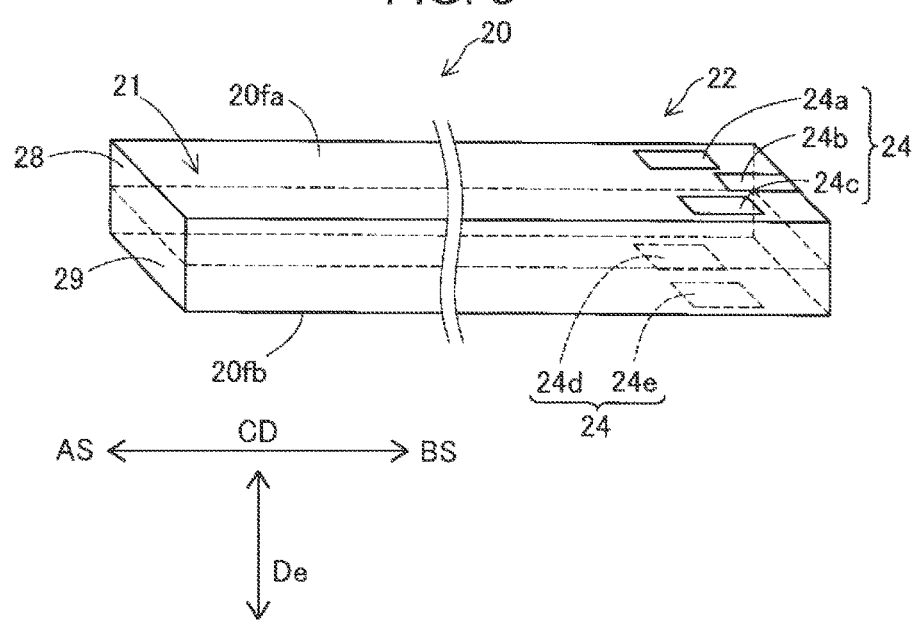
FIG. 3 is a schematic diagram of a detector element.

FIG. 1 is a sectional view of a gas sensor 200 according to a first embodiment of the present invention. FIG. 2 is a perspective view of a terminal accommodation unit 10. FIG. 3 is a schematic perspective view of a detector element 20. In FIG. 1, a direction parallel to an axis O of the detector element 20 is defined as an axial direction CD, the upper side of FIG. 1 is defined as a back side BS of the gas sensor 200, and the lower side of FIG. 1 is defined as a front side AS of the gas sensor 200.

The gas sensor 200 (FIG. 1) is attached to, for example, an inlet system (for example, an intake pipe) of an internal combustion engine, and outputs a detection signal for detecting a concentration of a specific gas component (oxygen concentration) in intake gas that flows through the inlet system. The gas sensor 200 according to the present embodiment is used to measure the oxygen concentration in the intake gas. The oxygen concentration is used, for example, to control the air-fuel ratio of an engine. A portion of the gas sensor 200 at the front side AS is disposed in the intake pipe.

The gas sensor 200 includes the terminal accommodation unit 10, an attachment 15, a metal shell 16, and a protector 17, which are arranged in that order from the back side BS toward the front side AS. The gas sensor 200 also includes the detector element 20 that extends in the axial direction CD.

The detector element 20 (FIG. 3) is plate shaped, and has a first principal surface 20fa and a second principal surface 20fb that oppose each other. The first principal surface 20fa and the second principal surface 20fb serve as principal surfaces of the detector element 20. Each of the first principal surface 20fa and the second principal surface 20fb has the largest area among the outer surfaces of the detector element 20. The direction of thickness of the detector element 20 between the two principal surfaces 20fa and 20fb of the detector element 20 is referred to as a thickness direction De. The thickness direction De is orthogonal to the axial direction CD and is a direction in which the first principal surface 20fa and the second principal surface 20fb oppose each other.

The detector element 20 includes a detection portion 21 at the front side AS in the axial direction CD and an element back portion 22 at the back side BS in the axial direction CD. The element back portion 22 includes first to third electrical pads 24a to 24c formed on the first principal surface 20fa and fourth and fifth electrical pads 24d and 24e formed on the second principal surface 20fb. Each of the electrical pads 24a to 24e is made of a metal, such as platinum, or a conductive material and has a substantially rectangular surface. The second electrical pad 24b is located further toward the back side BS than the other electrical pads 24a, 24c, 24d, and 24e. The first to fifth electrical pads 24a to 24e are referred to as "electrical pads 24" when it is not necessary to distinguish them from each other. The detection portion 21 is used to detect the concentration of a specific gas component (for example, oxygen) in the measurement target gas. As illustrated in FIG. 1, the front section of the detector element 20 in which the detection portion 21 is provided is covered with a detecting-portion protecting layer 90 formed of a porous material. The detecting-portion protecting layer 90 has a function of preventing water or the like contained in the measurement target gas from adhering to the detection portion 21.

The detector element 20 (FIG. 3), which is used as an air-fuel ratio sensor, has a structure similar to that of a detector element of the related art. Therefore, detailed description of the inner structure, for example, of the detector element 20 will be omitted, and the rough structure will be described. The detector element 20 has a multilayer body obtained by stacking a plate-shaped element layer 28, on which the detection portion 21 is formed, and a plate-shaped heater layer 29 for heating the element layer 28. The element layer 28 is formed by stacking assemblies, which each include a solid electrolyte body containing zirconia as the main component and a pair of electrodes containing platinum as the main component, with an insulating layer interposed therebetween, the insulating layer having a hollow measurement chamber formed in a portion thereof. The element layer 28 includes an oxygen pump cell and oxygen concentration measurement cell. The oxygen pump cell configured such that one of the pair of electrodes formed on both surfaces of the solid electrolyte body (hereinafter referred to as "first electrode") is externally exposed and the other of the pair of electrodes (hereinafter referred to as "second electrode") is disposed in the measurement chamber. And, the oxygen concentration measurement cell configured such that one of the pair of electrodes formed on both surfaces of the solid electrolyte body is disposed in the measurement chamber and the other of the pair of electrodes is disposed in a reference gas chamber. The element layer 28 controls a current that flows between the pair of electrodes of the oxygen pump cell so that an output voltage of the oxygen concentration measurement cell is a predetermined value. Owing to the current control, oxygen is discharged from the measurement chamber or introduced into the measurement chamber from the outside. The pair of electrodes and a portion of the solid electrolyte body sandwiched by the electrodes in the oxygen pump cell form the detection portion 21 through which a current corresponding to the oxygen concentration flows. The electrical pads 24 are used to transmit the detection signal from the detection portion 21 and supply electric power to heating wires embedded in the heater layer 29.

The terminal accommodation unit 10 (FIG. 1) includes a separator 30, which has a cylindrical shape with a bottom and includes a bottom portion 31 at the back side BS, and a connector portion 50 that extends from the separator 30 in a direction that crosses the axial direction CD. In the present embodiment, the connector portion 50 extends in the thickness direction De. The terminal accommodation unit 10 is formed of a resin material by integral molding. The resin material may be a highly formable resin, such as nylon (registered trademark), polyamide (PA), polybutylene terephthalate (PBT), or polyphenylene sulfide (PPS).

The separator 30 (FIG. 2) further includes first to fifth terminal accommodation spaces 34a to 34e and an element accommodation space 34f that receive the detector element 20 and connection terminals 60 (will be described later), a partition wall 35 that separates the six accommodation spaces 34a to 34f from each other, and a main body 41 that surrounds the partition wall 35 so as to form an outer peripheral portion. As illustrated in FIG. 1, the partition wall 35 includes a plurality of plate-shaped members that extend from the bottom portion 31 to a location near the front end surface of the separator 30. The partition wall 35 separates the six accommodation spaces 34a to 34f from each other in a plane orthogonal to the axial direction CD. As illustrated in FIG. 2, each of the first to fifth terminal accommodation spaces 34a to 34e accommodates a corresponding one of first to fifth connection terminals 60a to 60e. The element accommodation space 34f accommodates the element back portion 22 of the detector element 20 and portions of the first to fifth connection terminals 60a to 60e (more specifically, portions of element contact portions of the first to fifth connection terminals 60a to 60e).

When the separator 30 is viewed from the front side AS, the element accommodation space 34f is located in a substantially central region of the cylindrical separator 30, and the first to fifth terminal accommodation spaces 34a to 34e are located further toward the outer side in the radial direction of the separator 30 than the element accommodation space 34f. The six accommodation spaces 34a to 34f are referred to as "accommodation spaces 34" when it is not necessary to distinguish them from each other. The first to fifth terminal accommodation spaces 34a to 34e are referred to as "terminal accommodation spaces 34A" when it is not necessary to distinguish them from each other. The first to fifth connection terminals 60a to 60e are referred to as "connection terminals 60" when it is not necessary to distinguish them from each other.

The main body 41 (FIG. 2) extends from the peripheral edge of the bottom portion 31 at the back side BS in the axial direction CD toward the front side AS in the axial direction CD. The main body 41 constitutes a side portion of the separator 30. As illustrated in FIG. 1, the partition wall 35 and the main body 41 are indirectly connected to each other by the bottom portion 31. In addition, as illustrated in FIG. 2, the partition wall 35 and the main body 41 are directly connected to each other at least at the front side AS.

The connector portion 50 (FIG. 1) accommodates conductive members 52 (more specifically, one end portion 54 of each conductive member 52) for transmitting the detection signal output from the detector element 20 to the outside. Five conductive members 52 are provided (only one of them is shown in FIG. 1) so that the number of conductive members 52 corresponds to the number of connection terminals 60. The conductive members 52 are insert-molded when the separator 30 and the connector portion 50 are molded by using a resin material.

The other end portion 56 of each conductive member 52 is in contact with a corresponding one of the connection terminals 60 in the first to fifth terminal accommodation spaces 34a to 34e, and is thereby electrically connected to the corresponding connection terminal 60. The one end portion 54 of each conductive member 52 is disposed in an opening 58 in the connector portion 50, and an external connector is inserted into the opening 58. Accordingly, the one end portion 54 of each conductive member 52 is electrically connected to a corresponding one of terminals included in the external connector. The detection signal output by the detector element 20 is transmitted through the external connector to an external circuit (external device) that calculates the oxygen concentration.

The metal shell 16 is a cylindrical component in which the detector element 20 is disposed. The metal shell 16 is made of a stainless steel, such as SUS430. The metal shell 16 surrounds the periphery of the detector element 20 around the axial direction CD. The metal shell 16 holds the detector element 20 such that the detection portion 21 of the detector element 20 projects therefrom at the front side AS and the element back portion 22 of the detector element 20 projects therefrom at the back side BS. The metal shell 16 includes a back-side outer peripheral portion 168 at the back side BS thereof, and the attachment 15 is attached to the back-side outer peripheral portion 168 by laser welding or the like. The metal shell 16 includes a front-side outer peripheral portion 167 at the front side AS thereof, and the protector 17 is attached to the front-side outer peripheral portion 167 by laser welding.

The gas sensor 200 (FIG. 1) further includes a ceramic holder 175, a powder-filled layer 173, and a ceramic sleeve 171. A crimping ring 157 is disposed between the ceramic sleeve 171 and a back end portion 164 of the metal shell 16.

The ceramic holder 175 and the ceramic sleeve 171 are made of alumina. The ceramic sleeve 171 and the ceramic holder 175 are cylindrical components having rectangular shaft holes that extend in the axial direction CD. The plate-shaped detector element 20 is inserted through the rectangular shaft holes in the ceramic sleeve 171 and the ceramic holder 175.

The ceramic holder 175 is located on the front side AS of the powder-filled layer 173. The ceramic holder 175 is retained by a ledge portion 169 located at the front side AS of the metal shell 16.

The ceramic sleeve 171 is located on the back side BS of the powder-filled layer 173. The ceramic sleeve 171 is a member that presses talcum powder, which is the material of the powder-filled layer 173, toward the front side AS. After the ceramic sleeve 171 is disposed in the metal shell 16, the back end portion 164 of the metal shell 16 is crimped radially inward and toward the back end surface of the ceramic sleeve 171, so that the ceramic sleeve 171 is fixed to the metal shell 16. The crimping ring 157 is disposed on the back side of the ceramic sleeve 171. The back end portion 164 of the metal shell 16 is crimped so that the crimping ring 175 presses the ceramic sleeve 171 against the powder-filled layer 173.

The powder-filled layer 173 is formed by filling the metal shell 16 with talcum powder, which is a powder material, and compressing the talcum powder. The detector element 20 extends through the powder-filled layer 173. The powder-filled layer 173 is disposed between the outer surface of the detector element 20 and the inner surface of the metal shell 16 so that the powder-filled layer 173 is in direct contact with the inner surface of the metal shell 16.

The metal shell 16 also has a groove portion 162 formed in the outer surface of the metal shell 16 so as to extend in the circumferential direction. A sealing member 158 that seals the space between the intake pipe and the metal shell 16 is disposed in the groove portion 162. In the present embodiment, the sealing member 158 is an O-ring. When the gas sensor 200 is attached to the intake pipe, the sealing member 158 is elastically deformed by being pressed against an inner wall of a sensor attachment hole in the intake pipe.

Owing to the elastic deformation of the sealing member 158, the space between the sensor attachment hole and the gas sensor 200 is sealed.

The protector 17 (FIG. 1) includes an outer protector 18 and an inner protector 19 disposed in the outer protector 18. The outer protector 18 and the inner protector 19 have a cylindrical shape with a bottom. Each of the outer protector 18 and the inner protector 19 is a metal member having a plurality of holes. The measurement target gas flows into the inner protector 19 through the holes. The outer protector 18 and the inner protector 19 cover the detection portion 21 of the detector element 20 to prevent water or the like that flows through a flow channel 84 from adhering to the detection portion 21.

The attachment 15 is a member that connects the metal shell 16 and the terminal accommodation unit 10. The attachment 15 is a component made of a metal, such as stainless steel. A portion of the attachment 15 at the front side AS is attached to the metal shell 16 by laser welding or the like, and a portion of the attachment 15 at the back side BS is attached to the main body 41 of the terminal accommodation unit 10 by crimping or the like. More specifically, a sealing member 159 is disposed in a groove 411 formed in the front end surface of the main body 41. The sealing member 159 is an O-ring. The sealing member 159 seals an attachment portion between the attachment 15 and the main body 41. The attachment 15 has a pair of flange portions (not shown) that project in the direction of the plane of FIG. 1. The flange portions have holes. Screws are inserted through the holes and screwed into threaded holes formed in the intake pipe, which is the object to which the gas sensor 200 is to be attached. Thus, the gas sensor 200 is attached to the object.

Figure 4A:
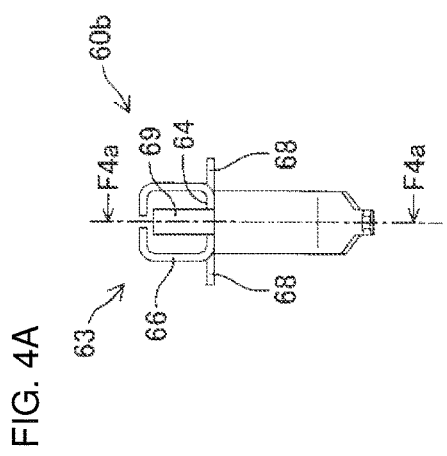
FIGS. 4A to 4D illustrate a second connection terminal.
Figure 4B:
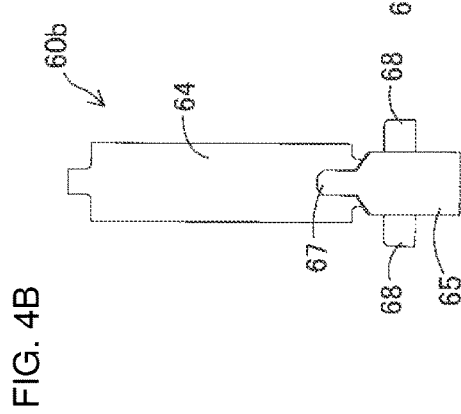
Figure 4C:
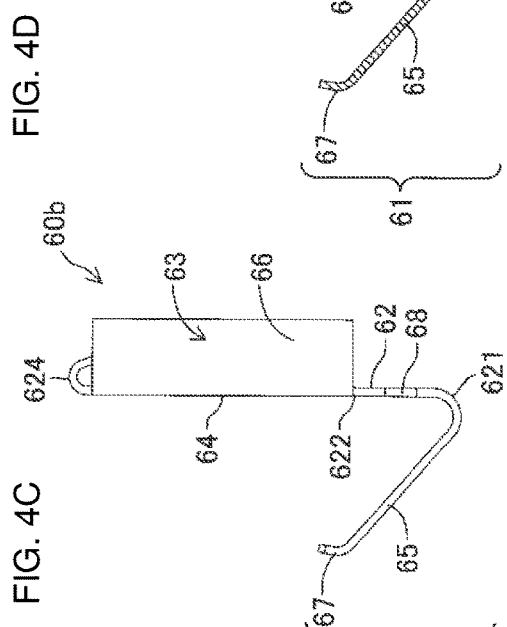
Figure 4D:
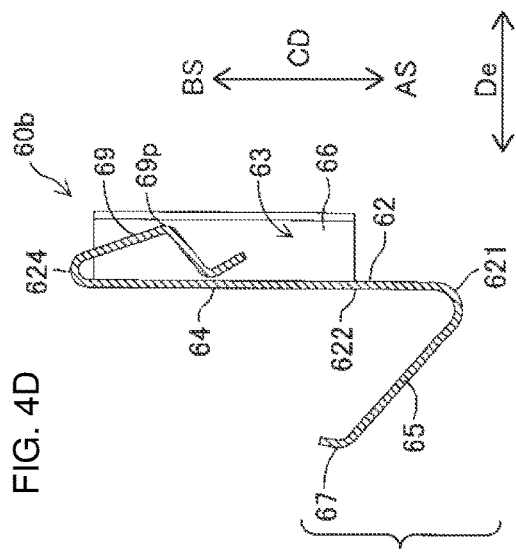

FIGS. 4A to 4D illustrate the second connection terminal 60b. FIG. 4A is a top view of the second connection terminal 60b. FIG. 4B is a front view of the second connection terminal 60b. FIG. 4C is a right side view of the second connection terminal 60b. FIG. 4D is a sectional view taken along line F4a-F4a in FIG. 4A. FIG. 4D shows the axial direction CD and the thickness direction De in the state in which the second connection terminal 60b is attached to the sensor 200.

As illustrated in FIG. 4D, the second connection terminal 60b includes a frame main body 62, an element contact portion 61, and a contacting portion 63. The frame main body 62 is oblong and extends in the axial direction CD. The frame main body 62 is a plate-shaped member. As illustrated in FIGS. 4B and 4C, the second connection terminal 60b further includes two projecting portions 68 provided on the frame main body 62. The two projecting portions 68 are disposed in grooves formed in the front end surface of the separator 30.

The element contact portion 61 is bent at a front end portion 621 of the frame main body 62 so as to extend toward the back side BS. More specifically, the element contact portion 61 is bent at the front end portion 621 so as to extend toward the detector element 20. The element contact portion 61 includes a spring portion 65 and an element contact 67. The spring portion 65 extends from the front end portion 621 toward the back side BS and the detector element 20. The spring portion 65 is a plate-shaped member. The element contact 67 is a portion of the spring portion 65 at the back side BS. The element contact 67 comes into contact with the second electrical pad 24b (FIG. 3). When the element contact 67 is in contact with the second electrical pad 24b, the element contact portion 61 is elastically deformed so as to approach the frame main body 62. Accordingly, the element contact portion 61 is in elastic contact with the second electrical pad 24b.

The contacting portion 63 is located on the back side BS of the frame main body 62. The contacting portion 63 includes a first contacting-portion main body 64, second contacting-portion main bodies 66, and a contacting terminal 69. The first contacting-portion main body 64 is a plate-shaped member that extends from a back end portion 622 of the frame main body 62 toward the back side BS. The second contacting-portion main bodies 66 are connected to both sides of the first contacting-portion main body 64 in the width direction (left-right direction in FIG. 4B). The second contacting-portion main bodies 66 are disposed on a side of the first contacting-portion main body 64 opposite to the side at which the element contact portion 61 is provided in the thickness direction De. As illustrated in FIGS. 4A to 4D, the second contacting-portion main bodies 66 are arranged so as to surround the contacting terminal 69 together with the first contacting-portion main body 64. In the present embodiment, the first and second contacting-portion main bodies 64 and 66 form a member having a frame-shaped cross section along a plane orthogonal to the axial direction CD. The contacting terminal 69 and the other end portion 56 of the corresponding conductive member 52 (FIG. 1) are disposed in the frame-shaped member.

In the present embodiment, the maximum dimension of the contacting portion 63 in the thickness direction De is substantially the same as the dimension of the terminal accommodation spaces 34A in the thickness direction De. As illustrated in FIGS. 1 and 2, the first contacting-portion main body 64 and the second contacting-portion main bodies 66 are accommodated in the second terminal accommodation space 34b. Accordingly, the first contacting-portion main body 64 and the second contacting-portion main bodies 66 are in contact with wall surfaces of the second terminal accommodation space 34b, so that the movement of the second connection terminal 60b (movement in a direction orthogonal to the axial direction CD) is restrained.

The contacting terminal 69 is bent at a back end portion 624 of the first contacting-portion main body 64 so as to extend toward the front side AS. The contacting terminal 69 is bent on a side of the frame main body 62 opposite to the side at which the element contact portion 61 is provided. The contacting terminal 69 includes a connector contact 69p, which comes into contact with the other end portion 56 of the corresponding conductive member 52 (FIG. 1), in a region surrounded by the first contacting-portion main body 64 and the second contacting-portion main bodies 66. Thus, in the thickness direction De, the element contact 67 and the frame main body 62 of the second connection terminal 60b are on the same side of the connector contact 69p (left side in FIG. 4D in the present embodiment).

FIGS. 5A to 5D illustrate the first and fifth connection terminals 60a and 60e. FIG. 5A is a top view of the first and fifth connection terminals 60a and 60e. FIG. 5B is a front view of the first and fifth connection terminals 60a and 60e. FIG. 5C is a right side view of the first and fifth connection terminals 60a and 60e. FIG. 5D is a sectional view taken along line F5a-F5a in FIG. 5A. FIG. 5D shows the axial direction CD and the thickness direction De in the state in which the first and fifth connection terminals 60a and 60e are attached to the sensor 200. The difference between the first and fifth connection terminals 60a and 60e and the second connection terminal 60b (FIGS. 4A to 4D) is the number of projecting portions 68 and the structure of an element contact portion 61a. The structures of other portions of the first and fifth connection terminals 60a and 60e are similar to those of the second connection terminal 60b. Therefore, similar portions are denoted by the same reference numerals and description thereof is omitted.

The number of projecting portions 68 is one (FIG. 5B). The projecting portion 68 projects in the width direction of a frame main body 62 at the front side AS of the frame main body 62. As illustrated in FIG. 5C, the element contact portion 61a is bent at a front end portion 621 of the frame main body 62 so as to extend toward the back side BS and toward the detector element 20. The element contact portion 61a differs from the element contact portion 61 of the second connection terminal 60b (FIGS. 4A to 4D) in that an inner extending portion 64a is provided and the width of a spring portion 65a is smaller than that of the spring portion 65 (FIGS. 4A to 4D).

The inner extending portion 64a extends from the front end portion 621 of the frame main body 62 toward the detector element 20 (so as to approach the detector element 20). The inner extending portion 64a according to the present embodiment extends in the horizontal direction, and is bent in the width direction of the frame main body 62 (left-right direction in FIG. 5B) at an intermediate position. In the first and fifth connection terminals 60a and 60e, the inner extending portion 64a is bent in a direction opposite to the direction in which the projecting portion 68 projects. In other embodiments, the inner extending portion 64a may extend obliquely relative to the horizontal direction.

The third and fourth connection terminals 60c and 60d (FIG. 2) differ from the first and fifth connection terminals 60a and 60e only in that the positions of the projecting portion 68 and the element contact portion 61a with respect to the frame main body 62 are opposite to those in the first and fifth connection terminals 60a and 60e. In other words, referring to FIG. 5B, in the third and fourth connection terminals 60c and 60d, the projecting portion 68 is on the left side of the frame main body 62 and the spring portion 65a is on the right side of the frame main body 62.

Figure 6:
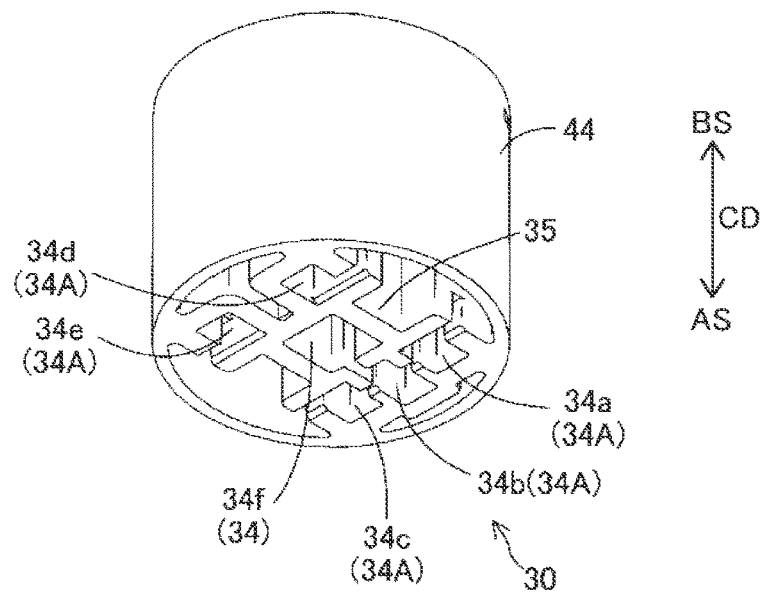
FIG. 6 is a schematic perspective view of a separator.
Figure 7:
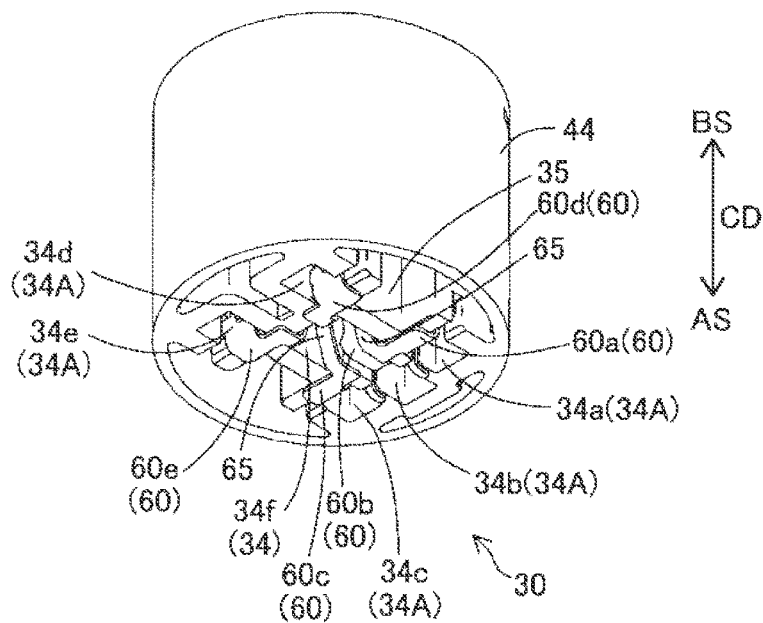
FIG. 7 is a schematic perspective view illustrating the state in which connection terminals are attached to the separator.
Figure 8:
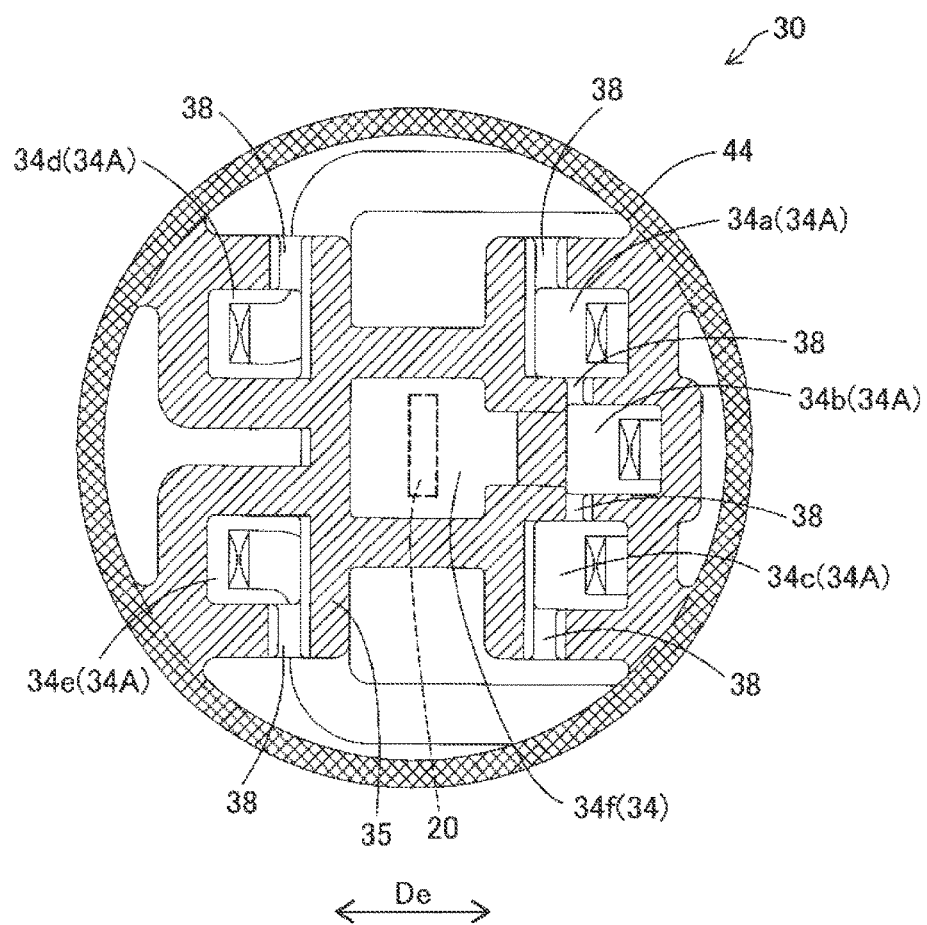
FIG. 8 illustrates the structure shown in FIG. 6 viewed from a front side.
Figure 9:
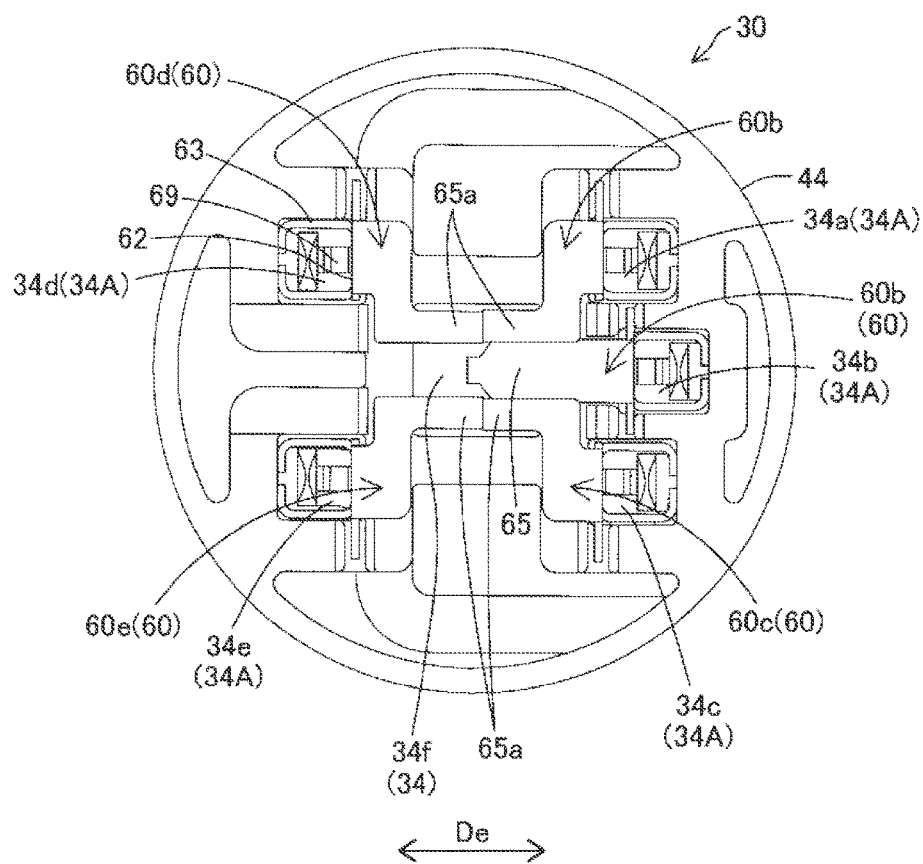
FIG. 9 illustrates the structure shown in FIG. 7 viewed from the front side.

FIG. 6 is a schematic perspective view of the separator 30. FIG. 7 is a schematic perspective view illustrating the state in which the connection terminals 60 are attached to the separator 30. FIG. 8 illustrates the structure shown in FIG. 6 viewed from the front side AS. FIG. 9 illustrates the structure shown in FIG. 7 viewed from the front side AS. FIGS. 6 and 7 illustrate a portion of the side portion 44 (FIG. 2) on the inner side of the groove 411 in the radial direction, and the structure of the side portion 44 is partially omitted. In FIG. 8, to facilitate understanding, the front end surface of the side portion 44 is shown as the cross-hatched area, the front end surface of the partition wall 35 is shown as the single-hatched area, and the location at which the detector element 20 is disposed is shown by the dashed line.

The separator 30 accommodates at least portions of the connection terminals 60 and at least a portion of the element back portion 22 (portion on which the electrical pads 24 are formed in FIG. 3). In the present embodiment, as illustrated in FIGS. 1 and 7, the separator 30 accommodates portions of the connection terminals 60 excluding portions at the front side AS. The separator 30 accommodates therein the contacting portions 63 and at last a portion of each conductive member 52 (other end portion 56 in FIG. 1).

The element accommodation space 34f accommodates the element back portion 22 of the detector element 20 and portions of the element contact portions 61 and 61a. Each terminal accommodation space 34A accommodates the frame main body 62 and the contacting portion 63 of the corresponding connection terminal 60 and the other end portion 56 of the corresponding conductive member 52. As illustrated in FIG. 8, each terminal accommodation space 34A is arranged next to the element accommodation space 34f in the thickness direction De.

The partition wall 35 includes a wall that separates the element accommodation space 34f and the terminal accommodation spaces 34A, which are arranged next to the element accommodation space 34f, from each other. The partition wall 35 separates the accommodation spaces 34 from each other so that each of the accommodation spaces 34 has a substantially rectangular cross section along a plane orthogonal to the axial direction CD. In other words, the partition wall 35 forms side walls of the accommodation spaces 34 that extend in the axial direction CD. Accordingly, when the connection terminals 60 and the detector element 20 are disposed in the separator 30, the peripheries of the frame main body 62 of each connection terminal 60 and the detector element 20 around the axial direction CD are surrounded by the partition wall 35. The front end surface of the partition wall 35 has grooves 38 that receive the projecting portions 68 of the connection terminals 60 (FIGS. 4B and 5B).

Figure 10:
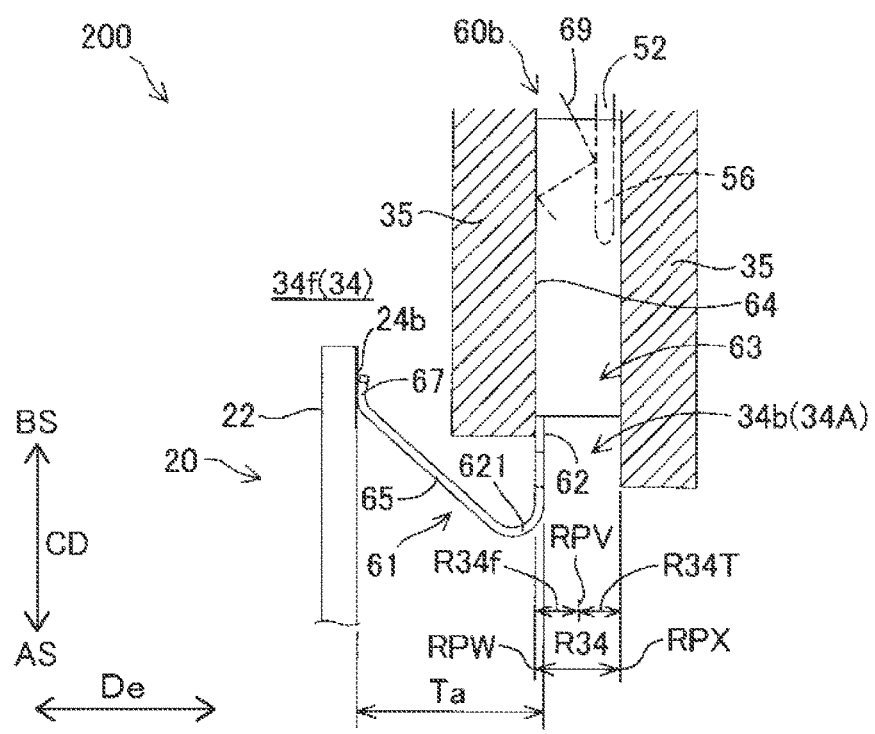
FIG. 10 is a diagram for further describing the gas sensor.

FIG. 10 is a diagram for further describing the gas sensor 200. Although the second terminal accommodation space 34b and the second connection terminal 60b will be described with reference to FIG. 10, the relationship described below also applies to the other terminal accommodation spaces 34a and 34c to 34e and the other connection terminals 60a and 60c to 60e.

The contacting portion 63 surrounds the conductive member 52 (more specifically, the other end portion 56) in the second terminal accommodation space 34b, thereby being in contact with the conductive member 52 so as to overlap the conductive member 52 in the thickness direction De. When the second terminal accommodation space 34b is extended toward the front side AS in the axial direction CD, the region in which the second terminal accommodation space 34b is located is defined as region R34. The region R34 is the region in which the second terminal accommodation space 34b is located when the gas sensor 200 is projected toward the front side AS in the axial direction CD onto a plane orthogonal to the axial direction CD. A portion of the region R34 on the side closer to the element accommodation space 34f in the thickness direction De is defined as an element-side region R34f. The element-side region R34f is a portion of the region R34 extending from the center RPV of the region R34 to an end RPW that is closer to the element accommodation space 34f in the thickness direction De. A portion of the region R34 on the side opposite to the side closer to the element accommodation space 34f in the thickness direction De is defined as an outer region R34T. The outer region R34T is a portion of the region R34 extending from the center RPV of the region R34 to the opposite end RPX in the thickness direction De.

The frame main body 62 is disposed in the element-side region R34f. In the present embodiment, the frame main body 62 is connected to the first contacting-portion main body 64, which is closest to the element accommodation space 34f in the thickness direction De in the contacting portion 63. In other words, the frame main body 62 is located near the end RPW in the element-side region R34f. The distance from the frame main body 62 to the element contact 67, which is in contact with the electrical pad 24b, in the thickness direction De is Ta.

Figure 11:
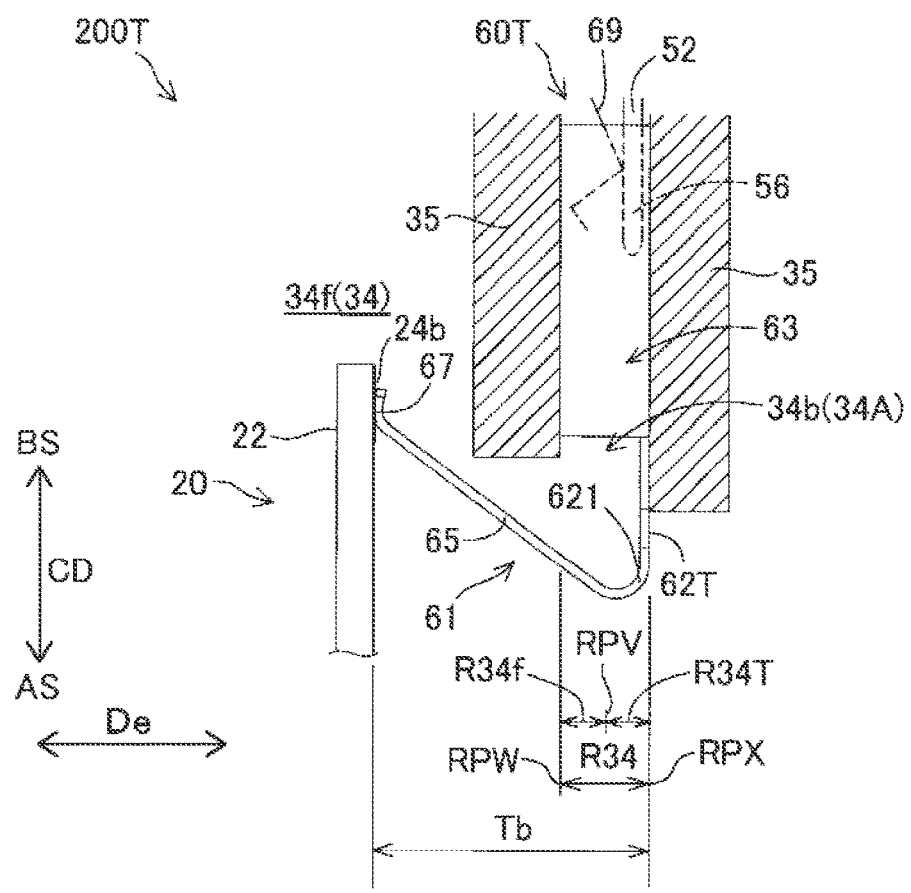
FIG. 11 is a diagram for describing a gas sensor according to a reference example.

FIG. 11 is a diagram for describing a gas sensor 200T according to a reference example. FIG. 11 corresponds to FIG. 10. The difference between the gas sensor 200T according to the reference example and the gas sensor 200 according to the present embodiment is the positions of frame main bodies 62 and 62T in the thickness direction De. Other structures of the gas sensor 200T are the same as those of the gas sensor 200. Therefore, similar portions are denoted by the same reference numerals, and descriptions thereof are thus omitted.

The frame main body 62T of the connection terminal 60T included in the gas sensor 200T is disposed in the outer region R34T of the region R34. In the reference example, the frame main body 62T is located near the end RPX in the outer region R34T. In other words, the frame main body 62T according to the reference example is connected to a portion of the contacting portion 63 that is farthest from the element accommodation space 34f in the thickness direction De. The distance from the frame main body 62T to the element contact 67, which is in contact with the corresponding electrical pad 24, in the thickness direction De is Tb.

As illustrated in FIGS. 10 and 11, in the gas sensor 200 according to the present embodiment, the frame main body 62 is disposed in the element-side region R34f. Accordingly, the distance from the frame main body 62 of the element contact portion 61 to the electrical pad 24b in the thickness direction De can be made smaller than that in the case where the frame main body 62a is disposed in the outer region R34T. In other words, the distance Ta (FIG. 10) can be made smaller than the distance Tb (FIG. 11).

Each of the element contact portions 61 and 61a (FIGS. 4A to 4D and 5A to 5D) is in contact with the corresponding electrical pad 24 while being elastically deformed such that the front end portion 621 serves as the starting point. In the present embodiment, since the distance Ta is small, the contact distance between the front end portion 621, which serves as the starting point of the elastic deformation of each of the element contact portions 61 and 61a, and the element contact 67 is small. Accordingly, when the element contact portion 61 and 61a comes into elastic contact with the corresponding electrical pad 24, a reduction in the pressing force applied to the electrical pad 24 can be suppressed. Since a reduction in the pressing force is suppressed, the occurrence of contact failure between each of the element contact portions 61 and 61a and the corresponding electrical pad 24 can be reduced.

In the present embodiment, the separator 30 is made of a resin material. Therefore, when the gas sensor 200 is in a high-temperature environment (for example, 150° C. or higher), there is a possibility that the separator 30, which is made of a resin material, will thermally expand. In such a case, when the separator 30 is configured such that the distance Ta is small before the thermal expansion thereof, the contact distance is prevented from becoming excessively large after the thermal expansion. More specifically, a reduction in the pressing force applied to each electrical pad 24 by the element contact portion 61 due to thermal expansion of the separator 30 can be suppressed.

B. Other Embodiments of Connection Terminals

Figure 12:
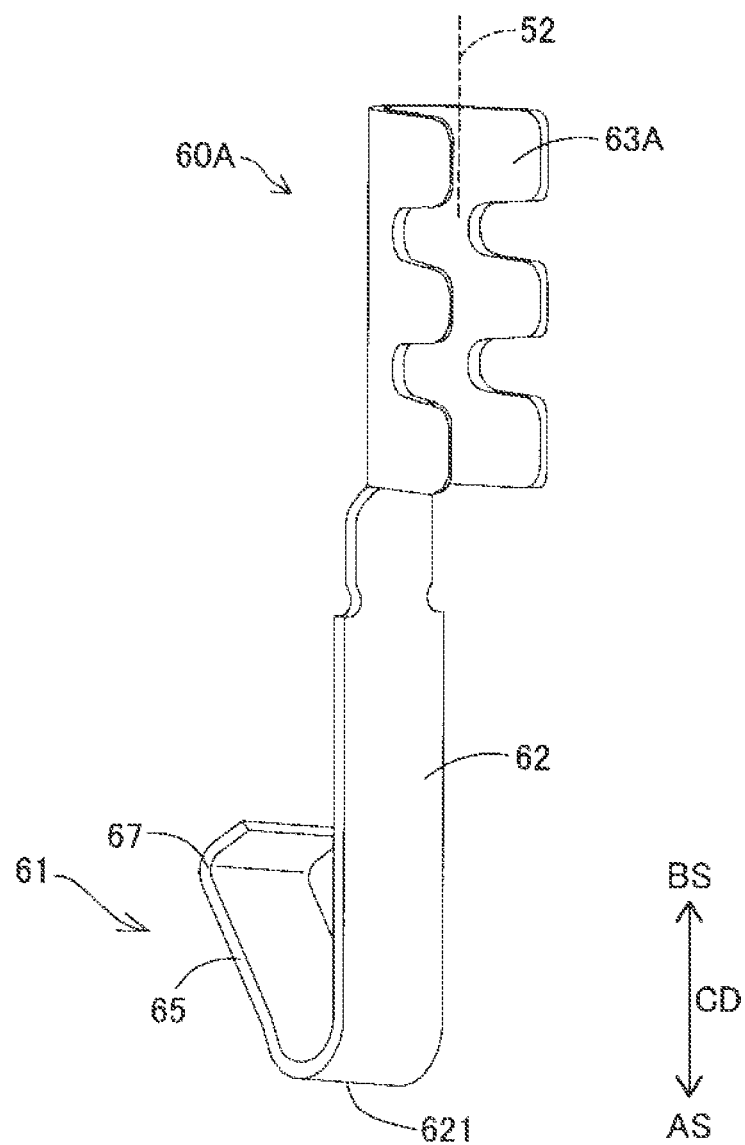
FIG. 12 is a perspective view of a connection terminal according to another embodiment.

FIG. 12 is a perspective view of a connection terminal 60A according to another embodiment. The shape of the contacting portion 63 of each connection terminal is not limited to that in the connection terminals 60a to 60e according to the above-described first embodiment (FIGS. 4A to 4D and 5A to 5D) as long as the contacting portion 63 surrounds the periphery of the conductive member 52 around the axial direction CD in the thickness direction De and thereby overlaps the conductive member 52 in the thickness direction De. For example, a connection terminal 60A illustrated in FIG. 12 includes a contacting portion 63A that comes into contact with the corresponding conductive member 52 when the contacting portion 63A is crimped inward after the other end portion 56 (FIG. 1) of the conductive member 52 is disposed in the contacting portion 63A. Similar to the first embodiment, the connection terminal 60A illustrated in FIG. 12 is also configured such that the frame main body 62 is disposed in the element-side region R34f (FIG. 10). Also in this case, similar to the above-described first embodiment, the distance Ta is small so that a reduction in the pressing force applied to each electrical pad 24 by the corresponding element contact portion 61 when the element contact portion 61 is in elastic contact with the electrical pad 24 can be suppressed.

In addition, in the above-described first embodiment, the contacting portion 63 of each connection terminal 60 surrounds the periphery of the other end portion 56 of the corresponding conductive member 52 so that the other end portion 56 and the contacting portion 63 overlap in the thickness direction De. However, the present invention is not limited to this. More specifically, one of the contacting portion 63 and the conductive member 52 may be arranged so as to surround the periphery of the other around the axial direction CD such that the contacting portion 63 and the conductive member 52 are in contact with each other so as to overlap in the thickness direction De. For example, the periphery of the contacting portion 63 may be surrounded by the other end portion 56 so that the other end portion 56 and the contacting portion 63 overlap in the thickness direction De. For example, the other end portion 56 is formed in a hollow shape, such as a tubular shape that extends in the axial direction CD, and the contacting portion 63 is formed in a linear shape that extends in the axial direction CD. The contacting portion 63 may be inserted into the other end portion 56, so that the other end portion 56 and the contacting portion 63 come into contact with each other in each terminal accommodation space 34A. Also in this case, by disposing the frame main body 62 in the element-side region R34f, the distance Ta can be reduced as in the above-described first embodiment. Accordingly, a reduction in the pressing force applied to each electrical pad 24 by the corresponding element contact portion 61 when the element contact portion 61 is in elastic contact with the electrical pad 24 can be suppressed.

C. Modifications

The present invention is not limited to the above-described embodiments, and may be implemented in various forms without departing from the gist thereof.

C-1. First Modification:

The gas sensors 200 according to the above-described embodiments are oxygen sensors that measure the oxygen concentration in the intake gas that flows through the intake pipe. However, the present invention is not limited to this, and may be applied to gas sensors for measuring the concentration of various types of specific gasses. For example, the gas sensors 200 may be sensors for measuring the concentration of Nox in the exhaust gas that flows through the exhaust pipe of an engine.

C-2. Second Modification:

The gas sensors 200 according to the above-described embodiments include five connection terminals 60 (FIG. 7). However, the number of connection terminals is not limited to this, and may instead be four or less or six or more. It is not necessary that the frame main body 62 be disposed in the element-side region R34f in all of the connection terminals

60 as long as the frame main body 62 is disposed in the element-side region R34f in at least one of the connection terminals 60. Also in this case, the connection terminal 60 in which the frame main body 62 is disposed in the element-side region R34f provides an effect similar to the effect of the above-described embodiments.

C-3. Third Modification:

The present invention is not limited to the above-described embodiments and modifications and may be embodied in various forms within the gist thereof. For example, the technical features of the embodiments and modifications corresponding to the technical features according to the aspects described in the Summary of the Invention section may be replaced or combined as appropriate to solve some or all of the above-described problems or obtain some or all of the above-described effects. The technical features may also be omitted as appropriate unless they are described as being essential in this specification.

REFERENCE SIGNS LIST

10: terminal accommodation unit
15: attachment
16: metal shell
17: protector
18: outer protector
19: inner protector
20: detector element
20fa: first principal surface
20fb: second principal surface
21: detection portion
22: element back portion
24: electrical pad
24a: first electrical pad
24b: second electrical pad
24c: third electrical pad
24d: fourth electrical pad
24e: fifth electrical pad
28: element layer
29: heater layer
30: separator
31: bottom portion
34: accommodation space
34A: terminal accommodation space
34a: first terminal accommodation space
34b: second terminal accommodation space
34c: third terminal accommodation space
34d: fourth terminal accommodation space
34e: fifth terminal accommodation space
34f: element accommodation space
35: partition wall
38: groove
41: main body
44: side portion
50: connector portion
52: conductive member
54: one end portion
56: other end portion
58: opening
60, 60A, 60T: connection terminal
60a: first connection terminal
60b: second connection terminal
60c: third connection terminal
60d: fourth connection terminal
60e: fifth connection terminal
61, 61a: element contact portion
62, 62a, 62T: frame main body
63, 63A: contacting portion
64: first contacting-portion main body
64a: inner extending portion
65, 65a: spring portion
66: second contacting-portion main body
67: element contact
68: projecting portion
69: contacting terminal
69p: connector contact
80: sealing member
90: detecting-portion protecting layer
157: crimping ring
158, 159: sealing member
162: groove portion
164: back end portion
167: front-side outer peripheral portion
168: back-side outer peripheral portion
169: ledge portion
171: ceramic sleeve
173: powder-filled layer
175: ceramic holder
200, 200T: gas sensor
411: groove
414: main body side portion
621: front end portion
622, 624: back end portion
AS: front side
BS: back side
CD: axial direction
De: thickness direction
O: axis
R34: region
R34T: outer region
R34f: element-side region
RPV: center
RPW, RPX: end
Ta, Tb: distance

The invention claimed is:

1. A sensor comprising:
a detector element that extends in an axial direction and has a shape of a plate having two opposing principal surfaces, the detector element including a detection portion at a front side in the axial direction and an element back portion at a back side in the axial direction, the detection portion detecting a specific gas component contained in measurement target gas, the element back portion having an electrical pad formed on at least one of the two principal surfaces;
a connection terminal which includes an oblong frame main body that extends in the axial direction, an element contact portion that is bent at a front end portion of the oblong frame main body so as to extend toward the detector element and toward the back side and that is in elastic contact with the electrical pad, and a contacting portion that extends from a back end portion of the oblong frame main body toward the back side and that is in contact with a conductive member that is electrically connected to an external circuit; and
a separator that accommodates at least a portion of the connection terminal and at least a portion of the element back portion,
wherein the contacting portion is in contact with the conductive member so as to overlap the conductive member in a thickness direction, which is a direction of thickness of the detector element between the principal surfaces, and wherein the separator includes a partition wall that separates an element accommodation space and a terminal accommodation space from each other, the element accommodation space accommodating a portion of the element contact portion and the element back portion, the terminal accommodation space accommodating the contacting portion and a portion of the conductive member and being adjacent to the element accommodation space in the thickness direction.

2. The sensor as claimed in claim 1, wherein the contacting portion surrounds a periphery of the conductive member or is surrounded by the conductive member at a periphery of the contacting portion, so that the contacting portion is in contact with the conductive member so as to overlap the conductive member in the thickness direction.

3. The sensor as claimed in claim 1, wherein the oblong frame main body is disposed in an element-side region, which is an inner region of the terminal accommodation space in the thickness direction.

4. The sensor as claimed in claim 3, wherein the element-side region is obtained by extending the terminal accommodation space toward the front side in the axial direction.

* * * * *